(12) United States Patent
Robins et al.

(10) Patent No.: US 7,119,246 B2
(45) Date of Patent: Oct. 10, 2006

(54) METHOD OF TREATING ACNE

(75) Inventors: Perry Robins, 330 E. 38th St., Suite 41N, New York, NY (US) 10016; Joseph G Sant'Angelo, 568 Parkside Ct., Allentown, PA (US) 18104

(73) Assignees: Perry Robins, New York, NY (US); Joseph G Sant'Angelo, Allentown, PA (US)

( * ) Notice: Subject to any disclaimer, the term of this patent is extended or adjusted under 35 U.S.C. 154(b) by 0 days.

(21) Appl. No.: 11/134,673

(22) Filed: May 23, 2005

(65) Prior Publication Data

US 2005/0208153 A1      Sep. 22, 2005

Related U.S. Application Data

(63) Continuation-in-part of application No. 10/178,522, filed on Jun. 25, 2002, now Pat. No. 6,909,027.

(51) Int. Cl.
*A61F 13/00* (2006.01)
*A01N 59/02* (2006.01)
*A01N 47/06* (2006.01)

(52) U.S. Cl. ............................ 602/48; 602/42; 602/52; 424/705; 514/28; 514/29; 514/512; 514/568

(58) Field of Classification Search ................ 424/705; 514/28, 29, 512, 568; 602/42, 48, 52
See application file for complete search history.

(56) References Cited

U.S. PATENT DOCUMENTS

| | | | | |
|---|---|---|---|---|
| 4,142,021 | A * | 2/1979 | Dixon et al. ................. | 428/412 |
| 4,833,036 | A * | 5/1989 | Cannarsa et al. ............ | 428/412 |
| 5,713,842 | A * | 2/1998 | Kay .............................. | 602/57 |
| 5,725,491 | A * | 3/1998 | Tipton et al. ................. | 602/43 |
| 6,034,113 | A * | 3/2000 | Hewawasam et al. ....... | 514/364 |
| 6,084,037 | A * | 7/2000 | Shimizu et al. .............. | 525/476 |
| 6,713,593 | B1 * | 3/2004 | Ree et al. ..................... | 528/196 |
| 7,022,346 | B1 * | 4/2006 | Tanaka et al. ............... | 424/489 |
| 2004/0038012 | A1 * | 2/2004 | Cook et al. ................... | 428/212 |
| 2005/0074474 | A1 * | 4/2005 | Sako ........................... | 424/401 |
| 2006/0018858 | A1 * | 1/2006 | Chen et al. .............. | 424/70.13 |

* cited by examiner

*Primary Examiner*—Kim M Lewis
(74) *Attorney, Agent, or Firm*—Thomas G. Ryder

(57) ABSTRACT

This invention relates to a method for the treatment of acne that comprises applying a fluid comprising a polyalkylene carbonate over the area affected by acne and penetrating pores within the area. Forming a polyalkylene carbonate film covering the affected area, and thereafter removing the film. The polyalkylene carbonate film can also contain medications useful in the treatment of acne.

18 Claims, No Drawings

METHOD OF TREATING ACNE

This application is a Continuation-in-Part of U.S. application Ser. No. 10/178,522, filed Jun. 25, 2002, now U.S. Pat. No. 6,909,027 the contents of which is hereby incorporated by reference.

This invention relates to a method for the treatment of acne utilizing a particular film forming material that will adhere to human skin.

BACKGROUND OF THE INVENTION

The ailment manifesting itself in eruptions of the skin, pimples, blackheads, whiteheads, lesions, cysts and nodules, and generally termed acne, has plagued people for generations. Acne typically develops in patients in their teen years, at the onset of puberty. While acne, per se, is not fatal, it results in disfigurement—mild or severe and temporary or permanent. At the very least, even the mild and temporary disfigurement of blackheads, whiteheads, papules and pustules is embarrassing and can result in social rejection by peers. Typically, acne affects most teenagers to some extent, but adults in their twenties through their forties can get acne. Although some type of mild acne is quite common among teenagers and most teenagers will "out grow" their acne by the time they are in their early twenties, acne is undesirable while it exists and can develop into more severe stages which can be permanently disfiguring because of the development of scars. There is also the possibility of the acne, particularly untreated acne, developing into more serious ailments because of infection.

In some instances mild cases of acne can be addressed by personal regimens as simple as twice daily washing with soap and warm water or the application of over-the-counter topical medications. In many cases, however, these simple, "home remedies" are inadequate. Part of the problem is that there can be different causes for the acne and many cases require the professional services of a dermatologist and the use of prescription medications.

Generally acne is the result of plugged pores caused by the accumulation of dirt, sebum, dead skin cells and *propionibacterium acnes* (*p. acnes*) in the pores, particularly in connection with hair follicles. A variety of over-the counter topical medications have been suggested in the past to deal with one or more of the factors contributing to acne and include, for example, the combination of isopropyl alcohol and acetone, benzoyl peroxide, resorcinol, salicylic acid and sulfur. Thus, in the combination of alcohol and acetone, the acetone functions as a degreasing agent and the alcohol has a mild anti-microbial effect. Benzoyl peroxide functions to reduce *p. acnes* and remove dead skin cells. Salicylic acid assists in the reducing the abnormal shedding of skin cells to help unplugging pores, but is not believe to have any impact upon *p. acnes* or sebum production. Sulfur has been used for many years, particularly in combination with other ingredients mention above. It is not understood how the sulfur operates, but due to the unpleasant odor of sulfur is usually not used alone. Thus, most of the over-the-counter topical medications do not address all of the possible contributing factors in the cause of acne.

In addition to the over-the-counter topical medications there are a variety of prescription medications that have been suggested for the treatment of acne. Among these prescription medications are topical antimicrobials and topical retinoids. Topical antimicrobials are designed to inhibit the growth of *p. acnes* and can be used either alone or in combination with medications that are effective against other causes of acne. The antimicrobials include, for example, azeliac acid, which is believed to function by reducing *p. acnes* populations, inflammation, and abnormal shedding of skin cells. Another antimicrobial is clindamycin, which works by reducing *p. acnes* and reducing inflammation. Similar to clindamycin is erythromicin, which is widely effective against bacteria, including *p. acnes*. Benzoyl peroxide (in higher doses than in over-the-counter medications) can also be sued, particularly in combination with erythromicin and clindamycin. Yet another antimicrobial medication is sodium sulfacetamide that inhibits *p. acnes* and opens clogged pores.

Topical retinoids (a derivative of vitamin A) function to unclog pores and prevent the formation of blackheads and whiteheads. Adapalene, which unclogs pores and has anti-inflammatory properties, is an example of a retinoid. Similarly, tazarotene and tretinoin function to unclog pores and keep them unplugged.

While some of the topical medicines discussed above are available in over-the-counter products, many of them are prescription medicines and/or require application by a dermatologist. Furthermore, topical medications have previously been limited to short term application due to the fact that they are "painted on" and then evaporate or wear off the skin rapidly.

In addition to the application of topical medications, it has also been suggested that "chemical peels" composed of chemical compounds such as glycolic acid can be used by dermatologists to loosen blackheads and decrease acne papules. While this technique has been effective to a greater or lesser extent, it has required that the patient return to a dermatologist for continued treatments.

We have discovered a method for treating acne which both permits practice of the method, in some instances, by an acne sufferer alone and, in other instances, provides a dermatologist with an improved method of treating acne patients.

BRIEF SUMMARY OF THE INVENTION

Our invention relates to a method for the treatment of acne that comprises applying a fluid comprising a polyalkylene carbonate (PAC) over the area of the patient's skin to be treated, thereby forming a film covering such area. Usually, the area involved is the area affected by acne, but it can include additional areas. The film is thereafter removed from the treated area. The polyalkylene carbonate fluid can also contain a medicament effective for the treatment of acne.

DETAILED DESCRIPTION OF THE INVENTION

The method of our invention for the treatment of acne comprises applying a polyalkylene carbonate in a fluid form over the area affected by acne or the area to be treated. The fluid polyalkylene carbonate applied to the area can be in the form of an emulsion, a suspension and a solution of the PAC in a biocompatible medium. The PAC can also be applied as a film which is raised to a temperature at least as high as the glass transition temperature of the PAC thereby causing the PAC to flow across the area and penetrate the pores in the area. In all instances the PAC forms a film covering the area to be treated. As the PAC, either with or without biocompatible suspension media, emulsion media or solvent, flows across the area to be treated and penetrates the pores in such area, any dirt, dead skin cells and bacteria are incorporated into the PAC film. Not only does the film form a barrier to external dirt, bacteria and skin cells, but any dirt, dead skin cells and bacteria (such as *p. acnes*) found already existing within pores in the area are incorporated into the PAC film. When the PAC film is thereafter removed from the area to be treated, it carries with it the dirt, oil, dead skin cells and bacteria incorporated into the film.

These effects are further enhanced when using emulsions, suspensions and solutions of PAC due to the fact that many of the biocompatible materials used have beneficial properties in themselves, such as, for example, the ability to dissolve oil, suspend dirt, and being mild bactericides.

Polycarbonates have been suggested as one of many polymers to be used as a film. They do not work as is taught in this application. Polycarbonates are different polymers than polyalkylene carbonates.

The recently developed family of polymers, called polyalkylene carbonates (PAC) are utilized to design the optimum environment and mechanism in and around the area to be treated. These polymers are produced by reacting carbon dioxide with epoxides. (Inoue S, "Organic and Bio-Organic Chemistry of Carbon Dioxide" Halsted Press, New York, pp 167–176, 1982) The resulting properties of the polymer are a function of the epoxide selected.

PAC polymers can be produced with properties that range from soft elastomeric with low glass transition temperatures (15° C. to 25° C. to 40° C.), to hard stiff polymers with high glass transition temperatures, e.g. 132° C. Intermediate properties can be produced by chemical (terpolymers) and physical (blends) means.

Films made from these polymers adhere to skin forming a barrier to outside dirt, water, and bacteria, penetrate the pores of the area being treated and result in any dirt, oil, dead skin cells and bacteria (e.g., *p. acnes*) in the treated area being incorporated into the film. Upon removal from the treatment site, the film also removes the materials incorporated into it, thereby removing materials known to be a cause of acne.

These films will not adhere to any open sores or wounds in the treated area, thereby permitting frequent dressing changes without disturbing the normal healing process of the area affected by acne. Additionally, these PAC polymers can be dissolved in a number of biologically acceptable solvents providing solutions of one or more polyalkylene carbonates with one or more solvents to permit designing the appropriate fluid, including foams or gels. These polymers can also be produced as water based emulsions. These solutions or emulsions can then be brushed or sprayed around the area to be treated, forming a conforming protective and interactive film to enhance treatment of acne. Other methods of application such as gels from squeeze tubes, melt formed films or liquid solutions rolled on or spread with a squeegee or spatula can be used. Other additives may be dissolved or dispersed in these fluids to permit design of a chemical medical system to enhance acne treatment. Acne treatment areas may first be pretreated with medical additives etc. then sprayed over with the film covering etc.

Physical and chemical properties of one or more of this family of polyalkylene carbonate polymers which can be selectively utilized are:

clear, amorphous, thermoplastic;
glass transition temperatures in the range of from about 15° C. to about 132° C.;
excellent adhesion to skin, non-sticking to wound;
soft, elastomeric polymers with good recovery, to hard engineering polymers;
low cost
quick drying with no odor;
soluble in a wide range of solvents from low boiling to high boiling;
low glass transition temperature of polyethylene carbonates, e.g. 20 to 25° C.;
makes for a soft, flexible and elastic film, which is softened by the skin and body temperature causing flow of the PAC and promoting conformability to body shapes in motion;
barrier to out side water, dirt, and bacteria; and
can be produced as water based emulsions.

The polyalkylene carbonates used in our invention can be dissolved in a biocompatible solvent or solvents. Some of the solvents that can be used include methylene chloride, dichloroethane, propylene carbonate, dimethylformamide, N-Methyl pyrrolidone, acetone, ethyl acetate, tetrahydrofuran, methyl ethyl ketone as well as other ketones, esters, ethers, etc. The polymer concentration in the fluid is a function of the delivery system selected.

The area to be treated is first cleaned, and then any of the following methods of application can be used:

If a spray can (aerosol) or bottle spray is used, then a lower concentration of polymer is used to provide the proper viscosity for spraying and film forming on and around the treatment site. This concentration is also a function of the solvent selected and molecular weight. Polymer concentrations in this application are usually in the range of from about 3 to about 35% by weight of the solution.

If a brush, Q-tip, eye-dropper or rod are used, then an intermediate polymer concentration is used with proper viscosity to prevent the solution from running away from the area to be treated. Polymer concentrations in this application are usually range of from about 3 to about 50% by weight of the solution.

If a gel or squeeze tube is used, the polymer concentration can be higher. The gel can be applied directly and spread out to form a film on and around the area to be treated. Polymer concentration in this application is usually in the range of from about 20 to about 60% by weight of the fluid.

If a melt film is to be used, dispensed from a melt film forming device, the polymer concentration can be relatively high, e.g. up to about 100% by weight polymer minus any additives, e.g., absorbents, moisturizers, medications, plasticizers, etc.

If an emulsion is used, e.g., a water based emulsion, the polymer concentration can be maximized based upon other chemicals in the system. Polymer concentration can be in the range of from about 5 to about 60% by weight.

The films produced from any of the above methods have excellent adhesion to itself. Therefore, these films can be made to wrap completely around certain body parts, and to adhere to itself. Spraying on a film can provide better protection around treatment sites in odd shaped (irregular shapes) of the body, by providing a complete seal around the area or site.

The use of polyethylene carbonate with excellent oxygen barrier properties, low Tg of about 25° C., very high elongation and recovery, flexibility and elasticity provides excellent conformity and protection to irregular body shapes. The low Tg, permits body skin temperatures to soften the polymer further and better conform to irregular shapes, increasing the patients comfort and providing excellent protection to the treatment area. Film thickness can be from about 0.25 mils to greater than about 3.0 mils, e.g., about 3.5 mils.

A preferred method of practicing the method of our invention is to produce a solution containing of from about 5 to about 15% by weight polyethylene carbonate, based on the solution, in methylene chloride. The methylene chloride also functions to kill bacteria (p. acnes) and fungi. The area to be treated is washed or pretreated, then dried. It is then coated with the polymer solution, brush or spray, and allowed to dry. The drying process is a matter of minutes due to the low boiling point of the solvent, i.e. 39.7° C. The skin temperature is about 33° C., body temperature about 37° C., promoting evaporation of the solvent, and flow of the polymer, which has a glass transition temperature of about 20–25° C., thereby resulting in the flow of PAC into the pores in the area. The progress of treatment can be observed through the clear film. As film changes are required, the film is easily removed and new film applied.

In certain cases, external oxygen may be desired and, therefore, polypropylene carbonate can be used, since it is not a good oxygen barrier. By blending PAC polymers, e.g. polypropylene carbonate and polyethylene carbonate, either physically or chemically (terpolymer), intermediate properties can be obtained to optimize treatment.

There are no other polymer families that can incorporate the unique broad range combination of physical/chemical properties obtainable with this recently developed family of polymers, polyalkylene carbonates. They can be "tailored" to fit the application, thereby providing a better healing system, reducing scarring which adds to patient comfort, and reducing costs.

In practicing the method of our invention, it is desired that the PAC film covering the area to be treated be kept on the treated area for a period of at least a few minutes, for example from about 10 minutes. Usually, however the PAC covering is kept on the area to be treated for at least about one hour and preferably at least about two hours. Although the film can be allowed to remain on the affected area overnight, the main benefits are achieved within about four hours after application. Generally, we prefer to limit applications to periods of less than about six hours and preferably less than about four hours. While it is not believed that any harm will come to a patient by leaving the film on until it sloughs off with the normal sloughing of dead skin cells, such procedure appears to detract from the earlier removal of the film along with incorporated dirt, oil, bacteria and dead skin cells and the application of a new film.

The method of our invention also encompasses the inclusion in the PAC polymer fluid a medicament effective for the treatment of acne. Such medicaments include those suitable for topical administration, such as those discussed above. Thus, for example, over-the-counter medications can be incorporated into the PAC polymer fluid, when it is intended that the method of our invention be practiced by an acne sufferer. Conversely, prescription medications can be included in the PAC polymer film, when the method is being practiced by or under the direction of a dermatologist. Most commonly, the medicament selected is an antibacterial agent. Preferred medicaments include benzoyl peroxide, sulfur, resorcinol, erythromycin, and clindamycin.

While a variety of alkylene substituents can be employed in the PAC polymer of our invention to alter the properties of the final polymer or polymers, we prefer to utilize polymers having lower alkylene substituents containing less than about 12 carbon atoms and particularly less than about 10 carbon atoms. Typically, we employ PAC carbonates having from about 2 up to about 9 carbon atoms. Most frequently, we employ ethylene, propylene or butene as the alkylene substituent in the PAC polymers used in our invention.

EXAMPLES

Example 1

In this example a base solution of polyethylene carbonate having a glass transition temperature ($T_g$) of about 22° C. is dissolved in methylene chloride to provide a solution in which the polyethylene carbonate is present in a concentration of 12% by weight based upon the solution. Separate samples of the base solution are prepared and to some of the samples are added medications. The compositions of the various samples are set forth in Table 1, below

TABLE 1

| SAMPLE | MEDICATION | CONCENTRATION |
|---|---|---|
| A | None | 0 |
| B | 50-50 by vol mixture of isopropyl alcohol & acetone | 2 vol % |
| C | Benzoyl peroxide | 0.15 vol % |
| D | Resorcinol | 0.1 vol % |
| E | Salicylic acid | 1.5 wt % |
| F | Sulfur | 5 wt % |
| G | Isopropyl alcohol | 10 vol % |
|   | Sulfur | 5 wt % |
| H | Resorcinol | 0.15 vol % |
|   | Sulfur | 5 wt % |

Each of the above samples is then applied to an acne affected area on a patient's skin and allowed to remain there for a period of two hours and is then removed. After removal a reduction of blackheads and whiteheads is noticed with all Samples.

Similar samples (A through H) are prepared and applied to acne affected areas on the skin of patients at twenty-four hour intervals and allowed to remain there for two hour periods over the course of a one week test period. Sample A continued to loosen and eliminate blackheads and whiteheads and to decrease papules. Samples B through H are additionally effective to remove oil, provide an antimicrobial effect (particularly concerning p. acnes), control small lesions, and control abnormal; shedding of skin cells.

All of the above samples are suitable for over-the-counter use in treating mild cases of acne.

Example 2

In this example a base solution of polypropylene carbonate having a glass transition temperature ($T_g$) of 40° C. is dissolved in methylene chloride to provide a solution in which the polyethylene carbonate is present in a concentration of 15% by weight based upon the solution. Separate samples of the base solution are prepared and various prescription medications are added to the samples. The compositions of the various samples are set forth in Table 2, below.

TABLE 2

| SAMPLE | MEDICATION | CONCENTRATION |
|---|---|---|
| I | Erythromicin | 2% by wt. |
| K | Clindamycin | 1% by wt. |
| L | Azelaic acid | 20% by wt. |
| M | Sodium sulfacetamide | 10% by wt. |

TABLE 2-continued

| SAMPLE | MEDICATION | CONCENTRATION |
|---|---|---|
| N | Adapalene | 0.02% by wt. |
| O | Tazarotene | 0.1% by wt. |
| P | Tretinoin | 0.05% by wt. |
| Q | Benzoyl peroxide | 5–10% by wt. |
| R | Erythromicin | 5–10% by wt |
|   | Benzoyl peroxide | 5–10 $ by wt. |
| S | Clindamycin | 5–10% by wt. |
|   | Benzoyl peroxide | 5–10% by wt. |
| T | Sodium sulfacetamide | 5–10% by wt. |
|   | Sulfur | 5–10% by wt. |
| U | Hydrocortisone | 1–2.5% by wt. |
| V | Triamcinalone | 0.01% by wt. |
| W | Fluorocinalone | 0.01–0.025% by wt. |
| X | Urea | 25% by wt. |
| Y | Hydroquinone | 4% by wt. |

Each of the above samples is then applied to an acne affected area on a patient's skin and allowed to remain there for a period of three hours and is then removed. After removal a reduction of blackheads and whiteheads is observed with all Samples.

Similar samples (I through V) are prepared and separately applied to acne affected areas on the skin of patients at intervals varying from twenty-four hours to one week and allowed to remain there for three hour periods over the course of test periods varying from 6 to 8 weeks. In addition to loosening and removing blackheads and whiteheads and decreasing papules, Samples I through V are additionally effective to remove oil, provide an antimicrobial effect (particularly concerning *p. acnes*), control lesions, control abnormal shedding of skin cells, reduce inflammation, and open clogged pores.

All of the above samples require the use of prescription medications and, thus, are suitable for use by or under the direction of a dermatologist.

We claim:

1. The method for the treatment of acne that comprises applying a fluid comprising a polyalkylene carbonate over the area affected by acne, forming a film covering the affected area and thereafter removing the film from the affected area.

2. The method of claim 1 wherein the film covering the affected area is permitted to remain on the affected area for a period of time of at least about one hour.

3. The method of claim 1 wherein the polyalkylene carbonate comprising fluid also contains a medicament effective for the treatment of acne.

4. The method of claim 3 wherein the medicament is effective as an antibacterial agent.

5. The method of claim 3 wherein the medicament is selected from the group consisting of benzoyl peroxide, sulfur, resorcinol, erythromycin, and clindamycin.

6. The method of claim 1 wherein the polyalkylene carbonate is placed in fluid form by forming a suspension of the of the polyalkylene carbonate in a biocompatible medium, applying the fluid polyalkylene carbonate suspension to the affected area and evaporating the biocompatible medium.

7. The method of claim 6 wherein the content of the polyalkylene carbonate in the suspension is from 3% to 50% by weight and the suspension is applied to the affected area.

8. The method of claim 1 wherein the polyalkylene carbonate is placed in fluid form by forming an emulsion of the polyalkylene carbonate in a biocompatible medium, applying the fluid polyalkylene carbonate emulsion to the affected area and evaporating the biocompatible medium.

9. The method of claim 8 wherein the content of the polyalkylene carbonate in the emulsion is from about 5% to about 60% and the emulsion is applied to the affected area.

10. The method of claim 1 wherein the polyalkylene carbonate is placed in fluid form by forming a solution of the polyalkylene carbonate in a biocompatible solvent, applying the fluid polyalkylene carbonate solution to the affected area and evaporating the biocompatible solvent.

11. The method of claim 10 wherein the content of the polyalkylene carbonate in the solution is from about 5% to about 60% by weight and the solution is applied to the affected area.

12. The method of claim 10 wherein the biocompatible solvent for polyethylene carbonate comprises methylene chloride.

13. The method of claim 10 wherein the polyalkylene carbonate is polyethylene carbonate having a glass transition temperature of from about 20° C. to about 25° C., the biocompatible solvent is methylene chloride and the polyethylene carbonate is present in the solution in a concentration of from about 5 to about 15% by weight.

14. The method of claim 1 wherein the alkylene component of the polyalkylene carbonate contains from two to nine carbon atoms.

15. The method of claim 1 wherein the alkylene component of the polyalkylene carbonate is selected from the group consisting of ethylene, propylene and butene.

16. The method of claim 1 wherein the polyalkylene carbonate has a glass transition temperature (Tg) of from about 15 to about 40° C. in a fluid form.

17. The method for the treatments of acne that comprises applying a film comprising a polyalkylene carbonate to an area affected by acne, thereby raising the temperature of the polyalkylene carbonate film to a temperature at least as high as its glass transition temperature of the polyalkylene carbonate causing the polyalkylene carbonate to flow across the area and penetrate the pores in the area and thereafter removing the film from the affected area.

18. The method of claim 17 wherein the content of the polyalkylene carbonate in the film is at least about 90% by weight and the film is applied to the affected area.

* * * * *